United States Patent
Khanna et al.

(12)

(10) Patent No.: US 6,660,287 B1
(45) Date of Patent: *Dec. 9, 2003

(54) PREVENTION OF SPOILAGE OF PRODUCE USING ACIDIFIED EXPANDED AMORPHOUS ALUMINUM SILICATE IMPREGNATED WITH CHLORITE

(75) Inventors: Neeraj Khanna, Norman, OK (US); Theodore D. Head, Noble, OK (US); Bryan D. Lowery, Oklahoma City, OK (US)

(73) Assignee: Bio-Cide International, Inc., Norman, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/670,067

(22) Filed: Sep. 26, 2000

Related U.S. Application Data

(63) Continuation-in-part of application No. 09/251,051, filed on Feb. 18, 1999, now Pat. No. 6,132,748.

(51) Int. Cl.[7] .............................. A61K 9/00; A61K 9/01; A61K 33/14
(52) U.S. Cl. ...................... 424/405; 252/187.21; 422/5; 422/37; 424/76.8; 424/661
(58) Field of Search ....................... 435/262.5; 424/661, 424/76.8, 405; 422/5, 37; 252/187.21

(56) References Cited

U.S. PATENT DOCUMENTS

| 3,591,515 | A | * | 7/1971 | Lovely et al. ............... 252/187 |
| 4,547,381 | A | | 10/1985 | Mason et al. |
| 4,689,169 | A | | 8/1987 | Mason et al. |
| 4,986,990 | A | * | 1/1991 | Davidson et al. ........... 424/665 |
| 5,695,814 | A | | 12/1997 | Wellinghoff et al. |
| 5,888,419 | A | | 3/1999 | Casella et al. |

* cited by examiner

Primary Examiner—David M. Naff
Assistant Examiner—Deborah K. Ware
(74) Attorney, Agent, or Firm—Crowe & Dunlevy, P.C.

(57) ABSTRACT

Expanded amorphous aluminum silicate (EAAS) is used as a vehicle for a chlorite salt. This vehicle, when exposed to moisture, will release chlorine dioxide ($ClO_2$) for purposes of deodorization or microbial suppression. Thus, where a particular area or volume is to be deodorized or made less microbially contaminated, the EAAS-chlorite salt (most preferably sodium chlorite) is placed in the area or volume to be treated and moisture is permitted to interact with the material. The result of the moisture is to permit the chemical reaction (presumably acidification) of the chlorite salt to yield dioxide gas. While normal EAAS has some inherent acidity, the inherent acidity is low enough so that, even when a chloride salt is encapsulated in the EAAS and the resultant mixture exposed to moisture, $ClO_2$ release is very slow and over an extended period.

17 Claims, 1 Drawing Sheet

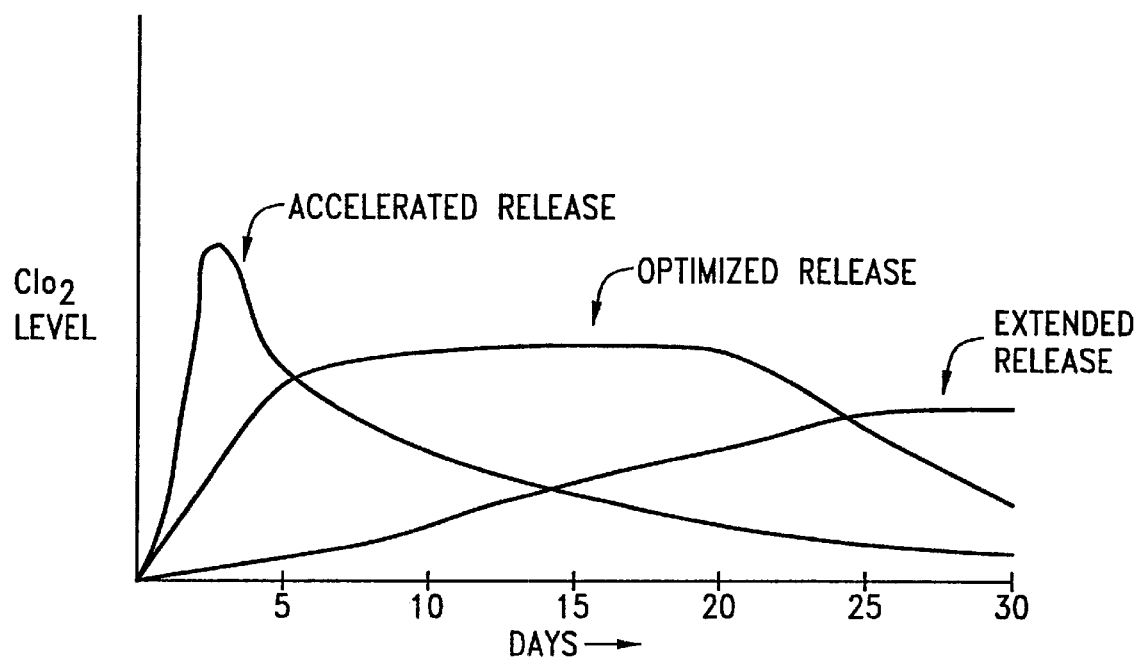

PREVENTION OF SPOILAGE OF PRODUCE USING ACIDIFIED EXPANDED AMORPHOUS ALUMINUM SILICATE IMPREGNATED WITH CHLORITE

RELATED APPLICATION

This application is a CIP of U.S. patent application Ser. No. 09/251,051, now U.S. Pat. No. 6,132,748, entitled METHOD FOR PRODUCING CHLORINE DIOXIDE USING CHEMICALLY IMPREGNATED EXPANDED AMORPHOUS ALUMINUM SILICATE, filed Feb. 18, 1999, and is hereby incorporated by reference.

FIELD OF INVENTION

The present invention relates to producing chlorine dioxide using expanded amorphous aluminum silicates ("EAAS") (CAS 93763-70-3).

BACKGROUND OF INVENTION

Chlorine dioxide ($ClO_2$) is a superior oxidizing agent widely used as a bleach, disinfectant, fumigant or deodorizer as it can penetrate the cell wall or membranes and cytoplasm of mold spores, bacteria and other microbiological contaminants at low concentrations.

The incorporation of chlorine dioxide or sodium chlorite in food packaging has prompted studies to determine whether residual levels of such preservatives result in a significant genetic or carcinogenic hazard to humans. Meier et al. studied the effect of subchronic and acute oral administration of chlorine, chlorine dioxide, sodium chlorite, sodium chlorate and related substances on the induction of chromosomal aberrations and sperm head abnormalities in mice. Only the highly reactive hypochlorite resulted in a weak positive effect for mutagenic potential. The other compounds, including chlorine dioxide and sodium chlorite, failed to induce any chromosomal aberrations or increased numbers of micronuclei in the bone marrow of mice. Richardson et al. reported that an extensive study of the reaction of chlorine dioxide with water borne organics by the Environmental Protection Agency confirmed this observation.

Japanese Patent Nos. 63/296,758, 63/274,434, and 57/168,977 issued to Kokai describe deodorants containing chlorine dioxide incorporated in a polymer, ceramic beads, and calcium silicate wrapped in non-woven cloth, respectively. Gels which generate chlorine dioxide for use as topical applications for disinfection are disclosed by Kenyon, et. al., Am. J. Vet. Res., 45(5), 1101 (1986). Chlorine dioxide generating gels are generally formed by mixing a gel containing suspended sodium chlorite with a gel containing lactic acid immediately prior to use to avoid premature chlorine dioxide release. Chlorine dioxide releasing gels have also been used in food preservation.

Encapsulation processes have also been used in preparing sources of chlorine dioxide. Canadian Patent No. 959,238 describes generation of chlorine dioxide by separately encapsulating sodium chlorite and lactic acid in polyvinyl alcohol and mixing the capsules with water to produce chlorine dioxide.

Tice, et al., U.S. Pat. No. 4,585,482; describe gradual hydrolysis of alternating poly(vinyl methyl ether-maleic anhydride) or poly(lactic-glycolic acid) to generate acid which can release chlorine dioxide from sodium chlorite. A polyalcohol humectant and water are encapsulated with the polyanhydride or polyacid in a nylon coating. After sodium chlorite is diffused into the capsule through the nylon wall, an impermeable polystyrene layer is coacervated around the nylon capsule. Solvents are required for reaction and application of the capsules. The capsules can be coated onto surfaces to release chlorine dioxide. Although the capsules are said to provide biocidal action for several days to months, chlorine dioxide release begins immediately after the capsules are prepared. The batchwise process used to prepare the capsules also involves numerous chemical reactions and physical processes, some of which involve environmental disposal problems. Wellinghoff, et. al., U.S. Pat. No. 5,695,814 describe methods of making a powdered biocidal composition for the release of $ClO_2$.

There is a need for a composite that can be easily activated to initiate chlorine dioxide release in use. A composition that is composed of and generates only FDA-approved substances, or those generally recognized as safe (GRAS), is particularly needed for food packaging and other applications where the substances can be ingested by or in contact with humans.

SUMMARY OF THE INVENTION

The present invention uses expanded amorphous aluminum silicate as a vehicle for a chlorite salt. This vehicle, when exposed to moisture, releases chlorine dioxide ($ClO_2$) for purposes of deodorization and microbial suppression, and for reducing spoilage and shrinkage for produce. Thus, where a particular area is to be deodorized or made less microbally contaminated, or where produce is to be treated, the EAAS-chlorite salt (most preferably sodium chlorite) is placed in the area to be treated and moisture is permitted to interact with the material. The moisture permits the chemical reaction (presumably acidification) of the chlorite salt to yield chlorine dioxide gas.

While normal EAAS has some inherent acidity, the inherent acidity is low enough such that, even when a chlorite salt is encapsulated in the EAAS and the resultant mixture exposed to moisture, $ClO_2$ release is very slow and over an extended period. Under most conditions, a more rapid release of $ClO_2$ is desired for deodorization and/or sterilization. A more rapid release of chlorine dioxide can be accomplished by first treating the native EAAS with an acid, preferably a protic acid, to acidify chemical groups of the EAAS. After native EAAS is acidified and dried, if necessary, a chlorite salt such as sodium chlorite is incorporated therein.

In another embodiment of the present invention, the chlorite salt is incorporated within the EAAS without prior acidification of the EAAS. In order to accelerate $ClO_2$ release, the EAAS-chlorite salt mixture may be exposed to a volatile acid such as acetic acid or the like. This may be prior to or in conjunction with the exposure of the EAAS incorporated chloride salt to moisture as found in water vapor or water droplets.

BRIEF DESCRIPTION OF THE DRAWINGS

The FIGURE shows $ClO_2$ release from accelerated release EAAS; optimized release EAAS; and extended release EAAS.

DETAILED DESCRIPTION OF THE INVENTION

EAAS can be synthesized by heating naturally occurring siliceous volcanic rock, known as Perlite. Perlite ore is extracted in the US and other countries, and is usually mined by scraping the earth's surface. Perlite is marketed by several companies, such as Incon Corporation of Media, Pa. and World Minerals, Inc. of Santa Barbara, Calif. Elemental analysis indicates that Perlite consists of 34% silicon and 7% aluminum, and Perlite therefore falls under the category of aluminum silicate minerals.

Perlite is chemically inert and has the ability to expand in volume by an order of magnitude when heated to certain temperatures, hence the adjective "expanded." To expand Perlite, Perlite crude is first crushed to a particle size of approximately ⅝ inch in a primary crusher. The crushed Perlite is then passed through an oil-fired rotary dryer, following which it undergoes a secondary grinding to produce the desired particle size. The heating temperatures range between 1400° and 2000° F., depending on water content and rate of heating. The word amorphous in EAAS is used to reflect the absence of a definite crystalline structure.

One form of EAAS used for the present invention is marketed by Paradigm International, Inc. of Irvine, Calif., under the brand name Stardust®. Another expanded Perlite product that is expected to behave similarly is Harbolite®, marketed by World Minerals Inc. of Santa Barbara, Calif. These products are moisturized forms of EAAS. Moisturization is performed to induce aggregates that preclude accidental inhalation.

The moisturized EAAS is soaked with an aqueous solution of from about 0.01% to about 40% chlorite anion by weight. In particularly preferred embodiments, the counterion is sodium, potassium or calcium; however any suitable source of the chlorite ion can readily be used in the alternative in accordance with the present invention. In a preferred embodiment, soaking can be achieved by spraying a 5% solution of sodium chlorite solution (such as ProOxine®, a product sold by BioCide International, Inc. of Norman, Okla.) while agitating the EAAS mechanically. The soaked EAAS is dried at a temperature of 120° C. for about two hours and sealed in an air-tight container or desiccator to prevent moisture absorption.

The activator is prepared in a similar manner by soaking EAAS in a protic acid solution. Any suitable protic acid may be used such as, without limitation, phosphoric, hydrochloric, sulphuric, nitric, acetic, citric, tartaric, glycolic, mandelic, salicylic, malic, maleic, aspartic, lactic or other structurally similar acids. Persons skilled in the art will recognize other suitable protic acids, all of which are intended to be suitable for use in the present invention. The concentration of the soaking solution can range from about 0.01 M to saturated, depending on the desired potency of the activator.

The chlorite impregnated EAAS and the acid impregnated EAAS can be combined in a specific ratio to release a desired concentration of chlorine dioxide. A preferred embodiment is to first acidify EAAS, and thereafter incorporate a chlorite salt into the acidified EAAS. In a particularly preferred embodiment, the mixture is packaged in a spin bonded olefin bag, such as a Tyvek® bag of appropriate porosity. Such bags are composed of porous material that allows moisture to diffuse into the bag while retaining the EAAS materials in the bag. Upon contact with moisture, the mixture releases $ClO_2$. Bags are best sealed from moisture until production of $ClO_2$ is desired, such as in a sealed plastic bag.

In certain uses, the chlorite-impregnated EAAS and the acid-impregnated EAAS can also be mixed on site to produce $ClO_2$, as opposed to premixing of the ingredients. Other suitable applications for the present invention will be readily recognized by those skilled in the art, all of which are within the spirit and scope of the present invention. For instance, in an alternative embodiment, a push/pull bottle can be used to store and activate the dry, chemically impregnated ingredients.

Although the present invention is not limited by a particular mechanism, a likely mechanism of $ClO_2$ release may be explained as follows. The water molecules in the moisture provide the medium that facilitates the interaction of chlorite ions with the protons. The chlorite ions probably reacts with the protons according to the following equation.

$$5ClO_2^- + 4H^+ \rightarrow 4ClO_2(g) + Cl^- + 2H_2O$$

One advantage of the present invention is the moisture-induced solid phase release of $ClO_2$ that creates an antimicrobial and deodorizing atmosphere at the site of application. In low ambient moisture environments, moisture can be fogged or otherwise applied from outside to accelerate $ClO_2$ production; however, normal humidity will usually supply the necessary moisture. The amorphous nature of the supporting phase provides a much longer time-range for sustained release of $ClO_2$ as compared to a support that is homogeneous in nature. This occurs due to the existence of a range of pore sizes (~10 to ~100 Å) in the amorphous substance that expands the kinetic time scale for the penetration of the water molecules.

The product can be used for the microbial control of dry or semi dry goods such as produce, cosmetics, medical devices, paper fabric, and fertilizers and other agricultural items. Also, this product can be used for odor control, since $ClO_2$ has been shown to exhibit excellent deodorizing properties.

The acid used to impregnate EAAS can be any suitable protic acid including the citric and salicylic acids mentioned in U.S. Pat. No. 6,132,748, referenced herein above, and which always are in a solid or powered form, or other protic acids such as succinic acid in the amorphous or powered form mentioned above. The activator can be prepared by simply exposing the EAAS to the liquid or powered protic acid to make an activator before mixing the activator with EAAS or the chlorite-impregnated EAAS. Acidified chlorine-impregnated EAAS also can be made by exposing chlorite-impregnated EAAS to liquid or powdered protic acid. Both methods were discussed in U.S. Pat. No. 6,132,748. These mixtures can be applied directly to the area or volume of produce or even soil with or without packaging. For example, the chlorite-impregnated EAAS could even be applied directly to the produce, soil, or compost for soil sanitation when growing mushrooms or other produce. Thus, as mentioned in U.S. Pat. No. 6,132,748, the chlorite-impregnated EAAS could be applied directly to produce, such as potatoes, onions, apples, and mushrooms or blown, such as by using an airstream, into an area holding the produce as discussed below.

An alternative to that explicitly mentioned in U.S. Pat. No. 6,132,748 is applying acid or activator (acid with EAAS) directly to the produce or blowing the acid or activator onto the produce and thereafter exposing the area to moisture by a misting chlorite solution to effect the release of chlorine dioxide gas.

An example of such use is for potatoes and other tubers, after harvest. Potatoes are typically stored for up to 10 months, and one of the biggest challenges for long-term potato storage is the prevention of spoilage from bacteria and fungi. Common potato spoilage can include soft rot (caused by *Erwinia carotovora*, for example), dry rot (caused by *Fusarium sambucinum*, for example), and silver scurf (caused by *Helminthosporium solani*, for example) which can be intensified by a fungus such as *Phytophthora infestans* which not only intensifies rot but can cause secondary infections (caused by *E. Carotovora*, for example) which can result in the collapse of potato piles in storage facilities.

It is well known that chlorine dioxide is quite effective in controlling all the above mentioned spoilage organisms. The efficacy data for Purogene a chlorine dioxide product (manufactured by Bio-Cide International, Norman, Okla.), against the organisms *Phytophthora infestans* and *Helminthosporium solani* is provided in the tables provided herein below in Example 7. Additional data including other organisms is available in Olsen et al., BUL 825, College of Agriculture, University of Idaho, 1999.

Currently, solutions of chlorine dioxide are being used in many storage facilities to prevent spoilage of potatoes. In most cases this practice has proved quite effective. However, in some situations where the harvested potatoes are too wet when placed into storage, this practice has not worked well. Spraying chlorine dioxide solution on already wet potatoes leads to extreme wetness which is believed to propagate late blight. Germination of *P. infestans zoospores* is facilitated in the presence of excess water, and the benefit of the biocidal power of chlorine dioxide is offset. In such situations a non-aqueous source of chlorine dioxide is desired.

The above described use of chlorine dioxide generation via EAAS works well on stored potatoes because this method does not require water. Additionally, since EAAS is water absorbent, it helps dry the wet tubers and facilitates disease management. Potatoes are typically stored under high moisture, a condition that helps the production of chlorine dioxide from EAAS as discussed above.

A specific embodiment is a 1:20 (wt/wt) of sodium chlorite and EAAS that can be applied to tubers moved over a conveyer belt of a piling machine. For potatoes that have high degree of infection, the release of chlorine dioxide from the chlorite/EAAS mixture can be accelerated by adding any acid in powder form such as citric or succinic. For efficient mixing of the acid with the chlorite/EAAS mixture, the acid can also be diluted with EAAS which can be mixed at the site of application.

This product can also be applied, with or without the activator, on piled potatoes in storage. The powder product can be blown into storage houses using an air stream through the plenum on as-required basis. Since most storage houses are designed to maintain high humidity, the chlorite/EAAS mixture releases chlorine dioxide when exposed to moisture. Also, since EAAS is generally mixed with agricultural soil as a porosity-enhancing diluent, the application of antimicrobial EAAS mixture is particularly useful on seed potatoes that require additional protection after planting in soil.

Currently, it is common practice to apply chlorine dioxide solutions in storage houses through humidification systems. Concentrated chlorine dioxide solutions are added in the humidification waters and the gas is carried by the vapor phase into potatoes piles. A major drawback of this approach is that due to the labile nature of the chlorine dioxide gas, most of the chlorine dioxide gas reacts with the tubers located on the surface of the pile and very little penetrates deeper. A separate embodiment of the present invention, as described here, provides a more efficient method for a homogeneous spread of the chlorine dioxide in the pile. In this embodiment, the potatoes are first sprayed with the activator powder (1 part citric acid: 5 part EAAS), following which the potatoes are piled as usual. Whenever application of chlorine dioxide is required, potatoes are fogged with sodium chlorite solution. Since sodium chlorite is much less reactive than the chlorine dioxide gas, penetration is deeper into the pile. After penetration, as the chlorite ions come in contact with the acidic activator powder on the surface of the tuber, reaction with the acid produces chlorine dioxide at the surface of individual tubers. Since chlorite ion is the limiting reagent, the piles can be fogged several times as required to produce spurts of biocidal chlorine dioxide gas. In this embodiment, EAAS is added in the activator solution for two reasons: 1) to prevent absorption of citric acid by the tuber, and 2) the protonation sites on the aluminum silicate molecule provides a medium for a sustain reaction.

EXAMPLE 1

EAAS is soaked with a protic acid. The amount of protic acid is in the range of 5 to 100% of the weight of EAAS. The exact quantity depends on the type of acid and the desired characteristics of the final product. In general, three different types of products can be manufactured. These are 1) accelerated release, 2) optimized release and 3) extended release. The $ClO_2$ release profiles for these products are shown in the Figure. To make product that will provide accelerated release, a greater amount of acid will be added. On the other hand, to make product that will provide optimized release, a lesser amount of acid will be added. On the other hand, to make product that will provide extended release, comparatively lower amounts of acid may be added, or the acid can be eliminated.

After soaking with acid, EAAS is baked in an oven at a temperature between 80° C. and 300° C. for several hours. The optimum temperature and time for baking is approximately 150° C. and two hours, respectively. The temperature condition can be varied to produce different types of products. For example, lower temperatures (about 100° C.) and short baking times (less than about 30 minutes) will produce product that will demonstrate accelerated release.

Subsequent to baking, solid sodium chlorite added to EAAS. The weight of sodium chlorite can range from 1 to 100% of the weight of EAAS. The weight of sodium chlorite is added to the EAAS depends on the desired characteristics of the product. In certain preferred embodiments, the quantity of sodium chlorite added to EAAS is between 4 to 15%. Thus the amount of acid, strength of acid and baking time are variables to produce desired patterns or $ClO_2$ release. Of course, the concentration and type of chlorite incorporated into the native or acid-treated EAAS can also be varied to produce desired $ClO_2$ release patterns.

The most commonly available form of sodium chlorite is the 80% pure form. One of the sources for such product is Vulcan Chemicals, Birmingham, Ala. Other sources and other purities of the preferred $NaClO_2$ may be used.

The EAAS used in the following examples was obtained from two different sources: 1) Paradigm International, Inc., CA and 2) Aldrich Chemical Company, Milwaukee, Wis. These materials are subsequently referred to as P1 and P2, respectively. The density of P2 is much higher than that of P1.

To monitor the level of free $ClO_2$ produced from the EAAS product, gallon jars made of poly(ethyleneterephthalate) commonly known as PET may be used. The EAAS product was packaged and used in a 50 cc wide-mouth bottle made of high density polyethylene (HDPE). The cap on the bottle had a push-pull mechanism for sealing or allowing the diffusion of air with the environment via an opening of 0.8 cm diameter. The $ClO_2$ gas that is generated by the product is discharged into the environment through this opening.

To measure the concentration of $ClO_2$ released from the EAAS product, the bottle was kept in the PET jar with a closed lid for a definite period of time and the $ClO_2$ levels were measured with a $ClO_2$-monitoring device commercially available as the Tox-Array 1000 apparatus manufactured by Mil-Ram Technologies, Inc., San Jose, Calif. This device was calibrated to measure from 0.1 to 20 ppm of $ClO_2$. For each measurement the sample was drawn from the top of the jar by opening the lid slightly and allowing the insertion of the sample suction tube into the jar. The suction tube was directly connected to the monitoring device.

The concentration of total available $ClO_2$ was measured by iodometric method 4500-$ClO_2$ B, described in the standard methods (19th Edition) of American Water Works Association.

The jars were kept in the ambient lab environment and the inside temperature was monitored. The temperature was between 20° C. and 25° C. The humidity inside these jars was maintained between 80% and 95% RH by spraying calculated amounts of water in the jars. The humidity was monitored with a hygrometer manufactured by Radio Shack (model 63-867A).

EXAMPLE 2

230 mL of 0.6M hydrochloric acid was sprayed on each of the 230 g of P1 and P2. These substances were sprayed with a generic spray bottle, with thorough stirring between every few sprays. The acidified EAAS was allowed to bake at 250° C. for one hour. The EAAS turned slightly brown in color, which was possibly due to oxidation of $Fe^{2+}$ to $Fe^{3+}$.

Two bottles of each P1 and P2 were kept in three different locations for trials of odor removal. The results are reported in Tables 1 and 2. Samples A and B were kept in a toilet facility (100 sq. ft.), samples B and C were kept in the laboratory (1,600 sq. ft.), and sample E and F were kept in an office (1,500 sq. ft.).

TABLE 1

Product made from P1
Free $ClO_2$ (ppm)

| Day | Incubation Time | Sample A | Sample B | Sample C | Sample D | Sample E | Sample F |
|---|---|---|---|---|---|---|---|
| 0 | 15 min | 6.4 | 6.5 | 6.5 | 6.6 | 6.4 | 6.5 |
| 1 | 15 min | 0.4 | 0.7 | 1.3 | 1.2 | 1.1 | 1.8 |
| 5 | 4 hours | 5.0 | 4.8 | 5.2 | 5.3 | 4.8 | 4.7 |
| 6 | 4 hours | 2.1 | 2.0 | 2.1 | 2.1 | 1.0 | 2.1 |
| 7 | 4 hours | 2.2 | 2.8 | 2.5 | 2.3 | 1.3 | 2.8 |
| 8 | 4 hours | 1.3 | 1.5 | 1.3 | 1.0 | 0.5 | 1.3 |
| 11 | 4 hours | 1.2 | 2.5 | 1.5 | 1.0 | 0.3 | 1.2 |
| 12 | 4 hours | 1.5 | 2.4 | 1.7 | 1.8 | 0.5 | 1.3 |
| 13 | 4 hours | 1.2 | 1.9 | 1.4 | 1.4 | 0.6 | 1.1 |
| 14 | 4 hours | 3.1 | 3.2 | 2.1 | 2.3 | 0.4 | 1.4 |
| 15 | 4 hours | 2.3 | 2.8 | 2.2 | 2.3 | 0.7 | 0.8 |
| 18 | 4 hours | 1.6 | 1.7 | 0.5 | 1.1 | 0.7 | 0.1 |
| 19 | 4 hours | 2.1 | 2.0 | 1.1 | 1.8 | 0.9 | 0.2 |
| 21 | 4 hours | 2.0 | 2.4 | 1.0 | 2.0 | 1.2 | 0.5 |
| 22 | 4 hours | 1.8 | 1.9 | 1.0 | 1.8 | 0.8 | 0.3 |

TABLE 2

Product made from P2
Free $ClO_2$ (ppm)

| Day | Incubation Time | Sample A | Sample B | Sample C | Sample D | Sample E | Sample F |
|---|---|---|---|---|---|---|---|
| 0 | 15 min | 9.8 | 9.9 | 9.7 | 9.9 | 9.8 | 9.8 |
| 1 | 15 min | 2.7 | 3.5 | 3.3 | 3.2 | 2.6 | 3.1 |
| 4 | 15 min | 0.3 | 0.9 | 0.8 | 0.8 | 1.0 | 0.9 |
| 5 | 1 hour | 4.3 | 4.0 | 3.0 | 3.3 | 2.3 | 3.0 |
| 6 | 1 hour | 0.9 | 2.1 | 1.5 | 1.4 | 1.1 | 1.5 |
| 7 | 1 hour | 0.9 | 2.0 | 1.4 | 1.3 | 0.5 | 1.2 |
| 8 | 1 hour | 0.5 | 1.4 | 1.4 | 0.5 | 0.4 | 0.7 |
| 11 | 1 hour | 0.4 | 1.2 | 0.9 | 1.0 | 0.3 | 0.7 |
| 12 | 1 hour | 0.8 | 1.5 | 1.2 | 1.1 | 0.6 | 1.1 |
| 13 | 1 hour | 1.1 | 1.5 | 0.8 | 0.7 | 0.3 | 1.1 |
| 14 | 1 hour | 3.3 | 3.2 | 2.0 | 1.8 | 0.9 | 1.6 |
| 15 | 1 hour | 4.1 | 3.1 | 1.6 | 1.4 | 0.4 | 0.6 |
| 18 | 1 hour | 3.8 | 3.5 | 0.7 | 1.3 | 0.9 | 0.7 |
| 19 | 1 hour | 5.1 | 4.9 | 1.5 | 2.1 | 2.3 | 1.7 |
| 21 | 1 hour | 3.9 | 4.8 | 3.0 | 3.5 | 3.1 | 1.1 |
| 22 | 1 hour | 2.5 | 3.6 | 2.1 | 2.5 | 1.9 | 0.9 |

EXAMPLE 3

Mencaptoethanol is a fundamental molecule that is one cause for odors from rotten food substances. We tested the effect of our product in eliminating the odor caused by this chemical substance. $25\mu$ of 1-mercaptoethanol (Aldrich) was tested by two PET jars of the type described above. In the first jar, a bottle containing 5 g of P1 was placed. The second control jar had no product placed in it. Lids sealed both jars. After 12 hours, the product bottle was taken out and the jars aired for 30 minutes. Subsequently, the jars were tested for mercaptan odor by 5 different individuals. None of them could detect any odor in the first jar, whereas the control-jar had a strong odor of mercaptan. The mechanism for the odor removal is believed to be the oxidation of the mercaptan by $ClO_2$.

EXAMPLE 4

The product is very effective in removing onion odors. 25 g of chopped white onions were stored in two PET jars overnight. The onions were removed the next day and the bottle with P1 product was placed in one of the jars. After 12 hours, the jars were inspected for odor by 5 different individuals. It was agreed that the odor was eliminated from the jar that was treated with the P1 product.

EXAMPLE 5

Four samples, each containing 5 g of P1, were treated with 0.5 mL, 1 mL, 3 mL and 5 mL of 0.6 M HCl. Similarly, four examples each containing 10 g of P2, were treated with 0.5 mL, 1 mL, 3 mL and 5 mL of 0.6 M HCl. These samples were allowed to air dry on the laboratory bench, and after one week. 0.5 g $NaClO_2$ was added. These samples were packaged in the 50 cc bottles described in a prior Example and the $ClO_2$ levels were monitored in the similar manner as earlier mentioned. In these cases the characteristics of $ClO_2$ release matched that of accelerated released as shown in the FIG. 1. The results are presented in the following Tables 3 and 4.

TABLE 3

Product made from P1
Free $ClO_2$ (ppm)

| Day | Incubation Time | 0.5 mL Acid | 1 mL Acid | 3 mL Acid | 5 mL Acid |
|---|---|---|---|---|---|
| 0 | 1 hour | 4.5 | 6.8 | 7.3 | 4.2 |
| 1 | 1 hour | 0.4 | — | — | — |
| 2 | 1 hour | 0.0 | 1.8 | — | — |
| 3 | 1 hour | — | — | 0.0 | — |
| 5 | 1 hour | — | 5.6 | — | — |
| 6 | 1 hour | — | 0.0 | — | 0.0 |

TABLE 4

Product made from P2
Free $ClO_2$ (ppm)

| Day | Incubation Time | 0.5 mL Acid | 1 mL Acid | 3 mL Acid | 5 mL Acid |
|---|---|---|---|---|---|
| 0 | 1 hour | 7.6 | 1.0 | 11.2 | 10.6 |
| 1 | 1 hour | 2.4 | 9.3 | — | — |
| 2 | 1 hour | — | 3.4 | — | — |
| 3 | 1 hour | — | — | 1.2 | — |
| 4 | 1 hour | — | — | — | — |
| 5 | 1 hour | 0.0 | 0.4 | — | — |
| 6 | 1 hour | — | 0.1 | — | — |

EXAMPLE 6

In this example, $NaClO_2$ is mixed with P1 and P2 that were not treated with any acid. The ratio of mixing was 0.5 g $NaClO_2$:5 g P1 and 0.5 g $NaClO_2$: 10 g P2. In these cases the characteristics of $ClO_2$ release matched those of extended release as shown in FIG. 1. The $ClO_2$ level released from the 50 cc bottle (described in Example 1) were below the detection limit of the Tox-Array monitoring device. However, when bulk amounts of both P1 and P2 formulations were left in the PET jars for approximately 1½ months, ~10 ppm and ~6 ppm of $ClO_2$ was detected, respectively.

EXAMPLE 7

Purogene can limit the growth of *Phytophthora infestans* and *Helminthosporium solani* as shown in the following results:

*Phytophthora infestans:*

1) Number of living sporangia after incubation at 7 C for 2 hrs.

| Purogene ppm | 1 | 2 | 3 | 4 | Average sporangia/mL |
|---|---|---|---|---|---|
| 100 | 0 | 0 | 0 | 0 | 0 |
| 50 | 0 | 0 | 0 | 0 | 0 |
| 25 | 0 | 0 | 0 | 0 | 0 |
| 12.5 | 0 | 0 | 0 | 0 | 0 |
| 6.25 | 0 | 0 | 0 | 0 | 0 |
| 3.25 | 4,000 | 2,000 | 0,0 | 0,0 | 3,000 |
| 0.0 | 9,000 | 12,000 | 9,000 | 11,000 | 10,250 |

2. Percent of germinated zoospores after incubation at 20 C for 24 and 48 hrs.

| Purogene ppm | 24 hrs (%) | 48 hrs (%) |
|---|---|---|
| 100 | 0 | 0 |
| 50 | 0 | 0 |
| 25 | 0 | 0 |
| 12.5 | 0 | 0 |
| 6.25 | 0 | 0 |
| 3.12 | 59 | 48 |
| 0.0 | 78 | 75 |

*Helminthosyorium solani:*

Percent germinated spores after incubation for 48 hrs at 20 C:

| Purogene ppm | Germinated spores (%) |
|---|---|
| 100 | 0.0 |
| 50 | 0.0 |
| 25 | 51.0 |
| 12.5 | 82.0 |
| 6.25 | 88.0 |
| 3.25 | 86.0 |
| 0.0 | 91.0 |

The following references as well as those separately cited above are incorporated in pertinent part by reference herein for the reasons cited:

1) Greenwood, N. N. Eamshaw, A. In Chemistry of the Elements; Pergamon Press: New York, 1989, pp399–416; 2) Perlite Institute Inc., 88 New Drop Plaza, Staten Island, NY 10306-2994; 3) Masschelein, W. J. In Chlorine Dioxide, Chemistry and Environmental Impact of Oxychlorine Compounds; Ann Arbor Science: Ann Arbor, 1979; 4) Wellinghoff, et. al., U.S. Pat. No. 5,695,814; 5) Tice, et al., U.S. Pat. No. 4,585,482; 6) Meier, et al., Environ. Mutagenesis, 7, 201 (1985); 7) Richardson, et al., Environ. Sci. Technol., 28, 592 (1994); and 8) Kenyon et al., Am. J. Vet. Res., 45(5), 1101 (1986).

It will be clear that the present invention is well adapted to attain the ends and advantages mentioned as well as those inherent therein. While presently preferred embodiments have been described for purposes of this disclosure, numerous changes may be made which will readily suggest themselves to those skilled in the art and which are encompassed in the spirit of the invention disclosed and as defined in the appended claims.

We claim:

1. A method for reducing spoilage of produce, the method comprising:
   placing an acidified Expanded Amorphous Aluminum Silicate (EAAS) impregnated with a chlorite salt in a selected area containing the produce; and
   exposing said area to moisture sufficient to generate $ClO_2$ to treat the selected area without the addition of an acid.

2. The method of claim 1, wherein the placing step further comprises:
   blowing the chlorite-impregnated EAAS on produce or soil.

3. The method of claim 2 wherein the produce is potatoes.

4. The method of claim 2 wherein the produce is mushrooms.

5. A method for producing a source of ClO$_2$, which is activated by moisture on produce and soil, comprising:
  treating Expanded Amorphous Aluminum Silicate (EAAS) with an acid:
  drying the acidified EAAS; and
  incorporating a chlorite salt into the dried acidified EAAS.

6. A method of treating soil, comprising:
  placing an EAAS on the soil, wherein the EAAS is an acidified, powdered EAAS containing a chlorite salt and an acid; and
  wherein the chlorite salt is sodium chlorite and the acid is a powdered protic acid.

7. The method of claim 6 wherein the soil is used to grow potatoes.

8. The method of claim 6 wherein the soil is used to grow mushrooms.

9. The method of claim 6 wherein the soil is compost used to grow mushrooms.

10. A method of producing a source of ClO$_2$ activatable by moisture on produce, the method comprising:
  impregnating a first portion of Expanded Amorphous Aluminum Silicate (EAAS) with a chlorite salt to produce a chlorite impregnated EAAS;
  impregnating a second portion of EAAS with an acid to produce an acid impregnated EAAS; and
  combining the chlorite impregnated EAAS with the acid impregnated EAAS to produce said source of ClO$_2$.

11. The method of claim 10 wherein impregnating the first portion of EAAS with chlorite salt comprises:
  spraying a five percent solution of sodium chlorite solution onto the first portion of EAAS and simultaneously agitating the first portion of EAAS.

12. A composition of matter useful for the production of chlorine dioxide on produce and soil comprising:
  an acid;
  a chlorite salt;
  a first quantity of Expanded Amorphous Aluminum Silicate (EAAS), wherein the first quantity of EAAS is impregnated with the chlorite salt; and
  a second quantity of EAAS, wherein the second quantity of EAAS is impregnated with the acid.

13. The composition of matter of claim 12 wherein the acid is citric acid.

14. The composition of matter of claim 12 wherein the acid is succinic acid.

15. The composition of matter of claim 12 wherein the acid is salicylic acid.

16. The composition of matter of claim 12 wherein the first quantity comprises a mixture of 1 part by weight of NaClO$_2$ and 20 parts by weight of EAAS.

17. The composition of matter of claim 16 comprising a mixture of the first and second quantity wherein the amount of acid is in the range of 5 to 100% by weight of NaClO$_2$ and 1 to 100% by weight of EAAS.

* * * * *

UNITED STATES PATENT AND TRADEMARK OFFICE
CERTIFICATE OF CORRECTION

PATENT NO. : 6,660,287 B1 Page 1 of 1
APPLICATION NO. : 09/670067
DATED : December 9, 2003
INVENTOR(S) : Neeraj Khanna It is certified that error appears in the above-identified patent and that said Letters Patent is hereby corrected as shown below:

Column 10:

Line 15, replace "Helminthosyorium" with, --Helminthosporium--.

Signed and Sealed this

Sixth Day of November, 2007

JON W. DUDAS
*Director of the United States Patent and Trademark Office*